United States Patent

Watts et al.

[11] Patent Number: 5,885,943
[45] Date of Patent: Mar. 23, 1999

[54] SULFUR BORON ANTIWEAR AGENTS FOR LUBRICATING COMPOSITIONS

[75] Inventors: Raymond F Watts, Long Valley; Ricardo A. Bloch, Scotch Plains; Jack Ryer, deceased, late of East Brunswick, by Rita Ryer, executrix; Roger K. Nibert, Hampton; James S. Puckace, Perrineville, all of N.J.

[73] Assignee: Exxon Chemical Patents Inc., Linden, N.J.

[21] Appl. No.: 993,619

[22] Filed: Dec. 18, 1997

[51] Int. Cl.$^6$ ...................... C10M 135/06; C10M 139/00
[52] U.S. Cl. ........................... 508/197; 558/295; 558/287
[58] Field of Search ............... 508/197; 558/295, 558/287

[56] References Cited

U.S. PATENT DOCUMENTS

| | | | |
|---|---|---|---|
| 2,346,156 | 4/1944 | Farrington et al. | 508/197 |
| 2,413,718 | 1/1947 | Lincoln et al. | 508/197 |
| 2,526,506 | 10/1950 | Rogers | 508/197 |
| 3,303,130 | 2/1967 | Scypinski et al. | 252/46.3 |
| 3,751,367 | 8/1973 | Clark et al. | 508/197 |
| 4,031,023 | 6/1977 | Musser et al. | 252/48.2 |
| 4,394,277 | 7/1983 | Small, Jr. | 252/32.7 |
| 4,465,605 | 8/1984 | Horodysky et al. | 252/46.3 |
| 4,492,640 | 1/1985 | Horodysky et al. | 252/46.3 |
| 4,689,162 | 8/1987 | Wirth et al. | 508/197 |
| 4,759,873 | 7/1988 | Audeh | 508/197 |
| 4,859,353 | 8/1989 | Colclough | 252/46.3 |

FOREIGN PATENT DOCUMENTS

| | | | |
|---|---|---|---|
| 0 216 909 | 2/1990 | European Pat. Off. | C10M 141/12 |
| 86/06092 | 10/1986 | WIPO | C10M 141/12 |
| 93/11137 | 6/1993 | WIPO | C07F 9/165 |

*Primary Examiner*—Margaret Medley
*Attorney, Agent, or Firm*—Ohlandt, Greeley, Ruggiero & Perle

[57] ABSTRACT

Sulfur-containing boroester compounds useful as antiwear additives for oleaginous compositions including alicyclic borate thioesters having the general formula (I):

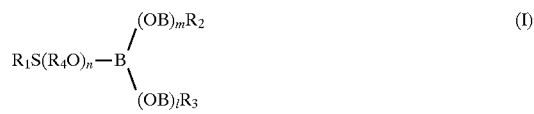

wherein $R_1$ is a hydrocarbyl radical having 4 to 12 carbon atoms, $R_2$ and $R_3$ are independently selected from —$(OR_4)_nSR_1$ and —$(OR_4)_nSR_1OH$; $R_4$ is a hydrocarbyl radical having 1 to 6 carbon atoms; n is an integer of from 1 to 4; and l and m are independently 0, 1 or 2; thioalkyl-substituted cyclic meta borate esters having the general formula (II):

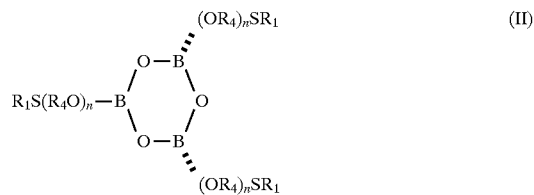

wherein n, $R_1$ and $R_4$ are defined as in formula (I); and mixtures of the alicyclic compounds of formula (I) and the cyclic compounds of formula (II).

15 Claims, No Drawings

SULFUR BORON ANTIWEAR AGENTS FOR LUBRICATING COMPOSITIONS

The invention relates generally to compounds useful as antiwear additives for oleaginous compositions. In particular, the present invention relates to alicyclic borate thioester and cyclic meta borate thioalkylester compounds suitable for use as antiwear additives for lubricating and power transmitting oils or fluids.

BACKGROUND OF THE INVENTION

Boron-containing compounds, and particularly borate esters are known to act as antiwear agents when added to lubricating oils. EP-A-0216909 discloses antiwear agents that are esters of metaboric acid, and have the following formula:

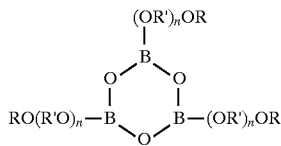

wherein each R is independently hydrogen or a hydrocarbyl group containing from 1 to 18 carbon atoms and each R' is independently an alkylene group containing from 2 to 4 carbon atoms.

It is further well known that sulfur-containing compounds act as anti-oxidants in lubricating compositions and can further enhance the effect of boron-based antiwear agents. The above described European Patent Specification discloses the use of the defined metaboric acid ester in combination with an oil soluble sulfurized organic compound in relative amounts sufficient to provide a weight ratio of sulfur to boron of from 0.5:1 to 20:1.

Antiwear agents providing both boron and sulfur are disclosed, for example, U.S. Pat. No. 3,303,130 describes an organo thioalkyl borate antiwear agent of the general formula:

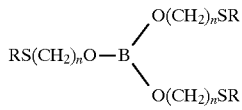

wherein R is selected from the group consisting of hydrogen, alkyl, aryl, alkaryl, aralkyl and cycloalkyl radicals containing 1 to 16 carbon atoms and n is an integer of 2 to 16, inclusive. These compounds are formed by reacting a thioalcohol with boric acid in a molar ratio of at least 3:1, and provide an antiwear additive having a weight ratio of sulfur to boron of 3.33:1. Similar compounds formed by reacting an alcohol, a hydroxysulfide and a boron compound, and the use thereof as a friction reducer in lubricating oil compositions are disclosed in U.S. Pat. No. 4,492,640.

Because of increased demand for lubricating oil additives and fierce competition between manufacturers, there has been a continued need for improved antiwear additives. The present inventors have developed an improved antiwear additive for lubricating oils which comprises a single compound that provides a relatively high weight ratio of boron to sulfur, while simultaneously providing antioxidant and friction modifier properties.

Other objects, advantages and features of the present invention will be understood by reference to the following specification.

SUMMARY OF THE INVENTION

The present invention, in brief summary, is directed to alicyclic thioalkyl borate esters of the formula (I):

wherein $R_1$ is a hydrocarbyl radical having between about 4 to 12 carbon atoms, $R_2$ and $R_3$ are independently selected from $-(OR_4)_nSR_1$ and $-(OR_4)_nSR_1OH$; $R_4$ is a hydrocarbyl radical having between about 1 to 6 carbon atoms; n is an integer of from between about 1 to 4; and l and m are independently 0, 1 or 2; (b) thioalkyl-substituted cyclic meta borate esters of formula (II):

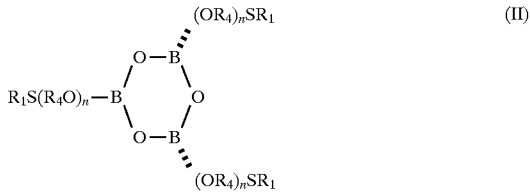

wherein n, $R_1$ and $R_4$ are defined as in formula (I); and (c) mixtures of the alicyclic compounds of formula (I) and the cyclic compounds of formula (II).

The present invention is further directed to lubricating oil and power transmitting oil compositions containing at least one antiwear agent selected from the group consisting of: alicyclic compounds of formula (I), cyclic compounds of formula (II), and mixtures thereof.

DESCRIPTION OF THE PREFERRED EMBODIMENTS

The alicyclic borate thioester and cyclic meta borate thioester antiwear additives of the present invention are the product of a condensation reaction of an alkoxyalkyl sulfide and boric acid in a molar ratio of at least about 1:1. Suitable alkoxyalkyl sulfides are compounds of formula (III):

wherein $R_1$ is a hydrocarbyl radical having between about 4 to 12 carbon atoms and $R_4$ is a hydrocarbyl radical having between about 1 to 6 carbon atoms. Preferable compounds of formula III include hydroxyethyldodecyl sulfide, 1-hydroxy-2-methyl-3-thio-decane and hydroxyethyloctyl sulfide (HEOS). The alkoxyalkyl sulfide can comprise a single compound or a mixture thereof.

When reacted with boric acid, the alkoxyalkyl sulfide will form a reaction product that can include both the alicyclic compound of formula I and the cyclic compound of formula II. The reaction strongly favors formation of the cyclic meta borate thioester and the reaction product may, in fact, contain only insignificant amounts, or essentially no, alicyclic borate thioester. The boric acid and hydroxalkyl sulfide are reacted in a molar ratio of about 1:1 or can be reacted in the presence of a slight molar excess of alkoxyalkyl sulfide (no greater than about 2:1). The reaction is conducted at a temperature within a range of from between about 0° to 150° C., preferably from between about 60° to 120° C., and at a pressure within a range from between about -100 to 0 kPa, preferably from between about -70 to -30 kPa.

The boric acid and hydroxalkyl sulfide may be reacted either neat or in an inert or non-participating polar solvent. Using hydroxyethyloctyl sulfide (HEOS) and boric acid reactants as examples, the reaction is believed to proceed as follows:

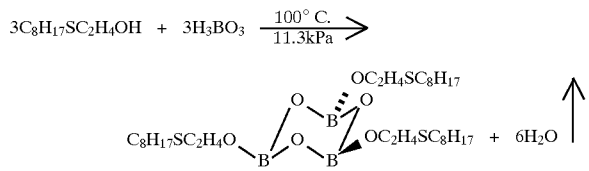

Lubricating oils and power transmitting oils to which the antiwear additives of the invention can be advantageously added are derived from natural oils, synthetic oils or mixtures of natural oils and synthetic oils. Suitable oils include base stocks obtained by isomerization of synthetic wax and slack wax, as well as base stocks produced by hydrocracking the aromatic and polar components of the crude.

Synthetic oils include hydrocarbon oils and halo-substituted hydrocarbon oils such as oligomerized, polymerized and interpolymerized olefins (e.g., polybutylenes, polypropylenes, propylene, isobutylene copolymers, chlorinated polyactenes, poly(1-hexenes), poly(1-octenes), poly(1-decenes), and mixtures thereof); alkylbenzenes (e.g., dodecylbenzenes, tetradecylbenzenes, dinonyl-benzenes, di(2-ethylhexyl)benzene); polyphenyls (e.g., biphenyls, terphenyls, alkylated polyphenyls); and alkylated diphenyl ethers, alkylated diphenyl sulfides, as well as derivatives, analogs and homologs thereof.

Synthetic oils also include alkylene oxide polymers, interpolymers, copolymers and derivatives thereof where the terminal hydroxyl groups have been modified by esterification, etherification, etc. This class of synthetic oils can be exemplified by polyoxyalkylene polymers prepared by polymerization of ethylene oxide or propylene oxide; as well as the alkyl or aryl ethers of these polyoxy-alkylene polymers (e.g., methyl-polyisopropylene glycol ether having a number average molecular weight of 1000 and diphenyl ether of polypropylene glycol having a number average molecular weight of about 1000 to about 1500); and mono- and poly-carboxylic esters thereof (e.g., acetic acid esters, mixed $C_3$ to $C_8$ fatty acid esters and $C_{12}$ oxo diester of tetraethylene glycol).

Another suitable class of synthetic lubricating oils comprises the esters of dicarboxylic acids (e.g., phthalic acid, succinic acid, alkyl succinic acids and alkenyl succinic acids, maleic acid, azelaic acid, subric acid, sebasic acid, fumaric acid, adipic acid, linoleic acid dimer, malonic acid, alkylmalonic acids and alkenyl malonic acids) with an alcohol (e.g., butyl alcohol, hexyl alcohol, dodecyl alcohol, 2-ethylhexyl alcohol, ethylene glycol, diethylene glycol monoethers and propylene glycol). Specific examples of these esters include dibutyl adipate, di(2-ethylhexyl) sebacate, di-n-hexyl fumarate, dioctyl sebacate, diisooctyl azelate, diisodecyl azelate, dioctyl isothalate, didecyl phthalate, dieicosyl sebacate, the 2-ethylhexyl diester of linoleic acid dimer, and the complex ester formed by reacting one mole of sebasic acid with two moles of tetraethylene glycol and two moles of 2-ethyl-hexanoic acid.

Esters useful as synthetic oils also include those made from $C_5$ to $C_{12}$ monocarboxylic acids and polyols and polyol ethers such as neopentyl glycol, trimethylolpropane pentaerythritol, dipentaerythritol, tripentaerythritol, and the like.

Silicon-based oils (such as the polyalkyl-, polyaryl-, polyalkoxy- or polyaryloxy-siloxane oils and silicate oils) comprise another useful class of synthetic oils. These oils include tetra-ethyl silicate, tetraisopropyl silicate, tetra-(2-ethylhexyl) silicate, tetra-(4-methyl-2-ethylhexyl) silicate, tetra-(p-tert- butylphenyl) silicate, hexa-(4-methyl-2-pentoxy)-disiloxane, poly(methyl) siloxanes and poly(methylphenyl) siloxanes. Other synthetic lubricating oils include liquid esters of phosphorous-containing acids (e.g., tricresyl phosphate, trioctyl phosphate, and diethyl ester of decylphosphonic acid), polymeric tetra- hydrofurans, poly-α-olefins, and the like.

Natural oils include animal oils, vegetable oils (e.g., castor oil and lard oil), petroleum oils, mineral oils, and oils derived from coal or shale. Mineral oils to which the antiwear additives of the invention can be added include all common mineral oil base stocks. This includes oils that are napthenic or paraffinic in chemical structure. The oils may be refined by conventional methodology using acid, alkali, and clay or other agents such as aluminum chloride, or they may be extracted oils produced, for example, by solvent extraction with solvents such as phenol, sulfur dioxide, furfural or dichlordiethyl ether, etc. They may also be hydrotreated or hydrorefined, dewaxed by chilling or by catalytic processing, or hydrocracked. The mineral oil may also be produced from natural crude sources or be composed of isomerized wax materials or residues of other refined processes.

The lubricating or power transmitting oils may be derived from unrefined oils, highly refined oils, re-refined oils or mixtures thereof. Unrefined oils are obtained directly from natural sources or synthetic sources (e.g., shale or tar sands bitumen) without further purification or treatment. Examples of unrefined oils include a shale oil obtained directly from a retorting operation, a petroleum oil obtained directly from distillation, or an ester oil obtained directly from an esterification process, each of which is used without further treatment. Refined oils are similar to unrefined oils except that the refined oils have been treated in one or more purification steps to improve one or more properties. Suitable purification techniques include distillation, hydrotreating, dewaxing, solvent extraction, acid or base extraction, filtration and percolation, all of which are known to those of ordinary skill in the art. Re-refined oils are obtained by treating used oils in processes similar to those used to obtain the refined oils. These re-refined oils are also known as reclaimed or reprocessed oils and are often additionally processed by techniques for removal of spent additives and oil breakdown products.

The compounds of the invention can be incorporated into lubricating oils and power transmitting oils as an antiwear additive in an amount from between about 0.001 to 5 wt. %, preferably from between about 0.001 to 1.5 wt. %, most preferably from between about 0.2 to 1.0 wt. %. The oleaginous materials may be formulated to contain other additives such as viscosity modifiers, auxiliary antioxidants, friction modifiers, dispersants, antifoaming agents, auxiliary antiwear agents, pour point depressants, detergents, rust inhibitors and the like.

Compositions containing the above additives are typically blended into base oils in amounts sufficient to provide their normal attendant function. Representative examples of amounts in which these additives are conventionally to lubricating oils are as follows:

| Additive | Wt. % (broad)* | Wt. % (preferred)* |
|---|---|---|
| Viscosity Modifier | .01–12 | .01–4 |
| Corrosion Inhibitor | .01–5 | .01–1.5 |
| Oxidation Inhibitor | .01–5 | .01–1.5 |

-continued

| Additive | Wt. % (broad)* | Wt. % (preferred)* |
|---|---|---|
| Dispersant | .1–20 | .1–8 |
| Pour Point Depressant | .01–5 | .01–1.5 |
| Anti-Foaming Agents | .001–3 | .001–0.15 |
| Anti-Wear Agents | .001–5 | .001–1.5 |
| Friction Modifiers | .01–5 | .01–3 |
| Detergents/Rust Inhibitors | .01–10 | .01–3 |
| Base Oil | Balance | Balance |

*active ingredient

The additives can be incorporated into the lubricating oil in any convenient manner. Thus, they can be added directly to the oil by dispersing or dissolving same in the oil. Such blending can be performed at room temperature or at elevated temperatures. Alternatively, the additives may be first formed into concentrates, which are subsequently blended with the oil. The final formulations may typically contain from between about 2 wt. % to 20 wt. % of additives.

Suitable dispersants include hydrocarbyl succinimides, hydrocarbyl succinamides, mixed ester/amides of hydrocarbyl substituted succinic acid, hydroxyesters of hydrocarbyl-substituted succinic acid, amides of aromatic acids and Mannich condensation products of hydrocarbyl-substituted phenols, formaldehyde and polyamines. Mixtures of such dispersants can also be employed. The dispersants may optionally be post treated with conventional reagents known in the art (see, e.g., U.S. Pat. Nos. 3,254,025; 3,505,677; and 4,857,214).

The preferred dispersant for use in combination with the sulfur boron antiwear additives of the present invention are alkenyl succinimides. These acyclic hydrocarbyl substituted succinimides are formed with various amines, polyamines and amine derivatives, and are well known to those of ordinary skill in the art. An example of a particularly suitable dispersant is the polyisobutenyl succinimide reaction product of polyisobutylene succinic anhydride, wherein the polyisobutene moiety preferably has a number average molecular weight in the range from between about 500 to 5000, preferably from between about 800 to 2500 and an alkylene polyamine such as triethylene tetramine or tetraethylene pentamine or mixtures of polyamines containing 3 to 12 nitrogen atoms per molecule, known in the art as PAM. The use of alkenyl succinimides that have been treated with an inorganic acid of phosphorus (or an anhydride thereof) and a boronating agent are also suitable for use in combination with the compounds of the invention and are more compatible with elastomeric seals made from such substances as fluoroelastomers and silicon-containing elastomers.

Suitable antioxidants for use in combination with the additives of the present invention include amine-type and phenolic antioxidants. Examples of amine-type antioxidants include phenyl alpha napthylamine, phenyl beta naphthalyamine and bis- alkylated diphenyl amines (e.g., p,p'-bis(alkylphenyl)-amines wherein the alkyl groups each contain from 8 to 12 carbon atoms). Phenolic antioxidants include sterically hindered phenols (e.g., 2,6-di-tert-butylphenol, 4-methyl-2,6-di-tert-butylphenol) and bis-phenols (e.g., 4,4"-methylenebis(2,6-di-tert-butylphenol). Phosphorous compounds, such as ZDDP, or phosphites are also commonly added to automatic transmission fluids (ATF) and passenger car motor oils (PCMO) as antioxidants. In addition to providing antiwear properties, the compounds of the present invention provide antioxidant credits to lubricating compositions, allowing for the formulation of lubricating compositions with a reduced amount, or no amount, of dedicated antioxidant additive.

Suitable friction modifiers are molecules having a polar head group and an oleophilic tail group. The polar head groups cause the molecule to be adsorbed onto the friction surface. These groups can be, but are not limited to, amines, mono and diethoxylated amines, carboxylic acids, amides, imides, alcohols, phenols, thiols, sulfonic acids, phosphites, phosphates, esters and combinations thereof. The oleophilic groups are typically alkyl groups, normally linear alkyl groups. These alkyl groups range in carbon number from between about $C_8$ to $C_{30}$, preferably from $C_{12}$ to $C_{20}$. They may be saturated or unsaturated, and may contain hetero atoms such as nitrogen or sulfur providing that the hetero atoms do not adversely affect the ability of the molecule to function as a friction modifier.

Examples of friction modifiers suitable for use with the antiwear additives of the invention include oleamide, tallow amine, diethoxylated tallow amine, N,N-bis(2-hydroxyethyl)-octadecyl amine, N,N-bis(2-hydroxyethyl)-stearyloxypropylamine, oleic acid, N,N-hydroxyethyl,N-(N',N'-bis(2-hydroxyethyl)ethylamine)-stearylamine and the diamide produced from isostearic acid and tetraethylene pentamine.

Suitable compounds for use as viscosity modifiers are generally high molecular weight hydrocarbon polymers, including polyesters. Oil soluble viscosity modifying polymers generally have weight average molecular weights from about 10,000 to 1,000,000, preferably from about 20,000 to 500,000, as determined by gel permeation chromatography or light scattering methods.

Representative examples of suitable viscosity modifiers are polyisobutylene, copolymers of ethylene and propylene and higher alpha-olefins, polymethacrylates, polyalkylmethacrylates, methacrylate copolymers, copolymers of unsaturated dicarboxylic acid and vinyl compound, inter polymers of styrene and acrylic esters, and partially hydrogenated copolymers of styrene/isoprene, styrene/butadiene and isoprene/butadiene, as well as partially hydrogenated homopolymers of butadiene and isoprene and isoprene/divinylbenzene.

Lubricating oils and power transmission oils incorporating the antiwear additives of the invention may also contain rust inhibitors such as nonionic polyoxyalkylene polyols and esters thereof, polyoxyalkylene phenols and anionic alkyl sulfonic acids, as well as corrosion inhibitors, such as thiadiazole polysulfides containing from between about 5 to 50 carbon atoms, their derivatives and polymers thereof; derivatives of 1,3,4-thiadiazoles; and thio and polythio sulfenamides of thiadiazoles. Such oils may also contain an antifoamant, including polyacrylate-type antifoamants, polysiloxane-type antifoamants and fluorosilicone-type antifoamants, and detergents, such as overbased and neutral calcium sulfonate, calcium phenate, magnesium sulfonate and magnesium phenate.

EXAMPLES

Synthesis Example 1

In a 5 liter, three neck flask, 2280 grams of hydroxyethyloctyl sulfide (12 mol) and 744 grams of boric acid powder (12 mol) are combined. The flask is equipped with a stirrer, a thermometer and a condenser that is connected to vacuum. The flask is heated to 110° C., and pressure within the flask is reduced to −70 kPa. After a few minutes water begins to evolve. The temperature in the flask is allowed to fall to 100° C. at which point heating is terminated and the exothermic reaction proceeds unassisted until 2 molar equivalents of water evolve and are collected. Heat is then applied until one additional molar equivalent of water evolves and is collected.

The product was characterized by a combination of analytical techniques. HPLC separation analysis shows that one primary species was formed. $^{13}$C NMR Spectroscopy indicated that the material had a characteristic sharp single resonance associated with a borated alkoxy methylene carbon at 62.8(1 C) ppm relative to TMS. $^{11}$B NMR Spectroscopy shows only one boro-oxygen ester signal at −3 ppm relative to $H_3BO_3$. The simplicity of the carbon and boron NMR spectral result are indicative of a highly symmetric meta-boroester structure. Characteristic carbon signals associated with the incorporation of hydroxyethyloctyl sulfide were found at 33(1C), 31.8(1C), 31.2(1C), 29.6(1C), 28.8 (1C), 28.6(1C), 22.4(1C) and 13.6(1C).

Example 2

To demonstrate the ability of the compounds of the present invention to provide antiwear and antioxidant activity in lubricating oils, Additive Packages (Adpacks) A through G were formulated as shown below and added to a viscosity modified base oil at a 7 mass % treat rate to form formulated oils. The formulated oils were then subjected to LMOT testing (described below) to determine antioxidancy improvements, and FZG testing (Four Square Gear Test, ASTM-D-5 182) to determine antiwear activity.

The Laboratory Multiple Oxidation Test (LMOT) is used to measure the ability of lubricant compositions to resist heat and air oxidation. In the LMOT, 50 cc of a test lubricant, 2.2 g of iron filings, and 0.5 g of a 1% copper solution (Nuodex® Copper 82 copper naphthenate in mineral spirits made into a 1% solution by dissolution of Nuodex 8% copper in 100NLP oil (Exxon Chemical)). At a temperature of 150° C. ±2° C., air is passed through the sample (25 cc+2 cc/min.). One drop per day of the sample lubricant is placed on a blotter until sludge appears. The results of the LMOT are presented in terms of days until sludge is observed (days to failure).

Adpack A
3.5% borated PIBSA/PAM 950 Mw isobutylene (dispersant); 0.45% diphenylamine (antioxidant); 0.45% HEOS-meta borate ester of Example 1; 0.15% friction modifiers; 0.001% fluorinated silicone antifoamant; and 2.439% base stock oil (all pecentages given as mass %).

Adpack B
3.5% borated PIBSA/PAM 950 Mw isobutylene (dispersant); 0.45% diphenylamine (antioxidant); 0.45% HEOS-meta borate ester of Example 1; 0.50% tolyl triazole (corrosion inhibitor) 0.15% friction modifiers; 0.001% fluorinated silicone antifoamant; and 1.939% base stock oil (all pecentages given as mass %).

Adpack C
3.5% borated PIBSA/PAM 2200 Mw isobutylene (dispersant); 0.45% diphenylamine (antioxidant); 0.45% HEOS-meta borate ester of Example 1; 0.15% friction modifiers; 0.001% fluorinated silicone antifoamant; and 2.439% base stock oil (all pecentages given as mass %).

Adpack D
3.5% borated PIBSA/PAM 2200 Mw isobutylene (dispersant); 0.45% diphenylamine (antioxidant); 0.45% HEOS-meta borate ester of Example 1; 0.50% tolyl triazole (corrosion inhibitor) 0.15% friction modifiers; 0.001% fluorinated silicone antifoamant; and 1.939% base stock oil (all pecentages given as mass %).

Adpack E
3.5% borated PIBSA/PAM 950 Mw isobutylene (dispersant); 0.45% diphenylamine (antioxidant); 0.15% friction modifiers; 0.001% fluorinated silicone antifoamant; and 2.899% base stock oil (all pecentages given as mass %).

Adpack F
3.5% borated PIBSA/PAM 950 Mw isobutylene (dispersant); 0.45% diphenylamine (antioxidant); 0.92% HEOS-meta borate ester of Example 1; 0.15% friction modifiers; 0.001% fluorinated silicone antifoamant; and 2.899% base stock oil (all pecentages given as mass %).

Adpack G
3.5% borated PIBSA/PAM 2200 Mw isobutylene (dispersant); 0.45% diphenylamine (antioxidant); 0.92% HEOS-meta borate ester of Example 1; 0.50% tolyl triazole (corrosion inhibitor); 0.15% friction modifiers; 0.001% fluorinated silicone antifoamant; and 1.479% base stock oil (all pecentages given as mass %).

TABLE 1

|  | A | B | C | D | E | F | G |
|---|---|---|---|---|---|---|---|
| Viscosity at 100° C. (cS) | 8.2 | 8.2 | 8.8 | 8.9 | 8.0 | 8.6 | 10.0 |
| LMOT at 320° F. (days to failure) | 8.5 | 9 | 11 | 10 | 7 | 11 | 11 |
| FZG (failure stage) | — | — | — | 10 | 8 | 11 | 12 |

As shown by the data of Table 1, the addition of adpack D, containing 0.46 mass % HEOS meta borate ester, to the base stock oil, improved the FZG by two load stages compared to an oil formulated without the borate ester (Adpack E). The use of additional HEOS meta borate ester (Adpacks F and G) led to further improvement in antiwear properties. The results of the LMOT testing display the ability of the HEOS meta borate ester to simultaneously function as an antioxidant. Specifically, the data regarding Adpacks A through D, containing 0.46 HEOS meta borate ester, demonstrate an increased LMOT of 1.5 to 3 days compared to the oil formulated without the additive of the invention (Adpack E) The addition of Adpack F or G, which contained 0.92 mass % of the HEOS meta borate ester provided a four day increase in the LMOT result compared to the composition formulated with Adpack E.

Example 3

To demonstrate the results achieved when the additives of the invention are co-formulated with commonly used phosphorous-based additives, three oil compositions were formulated to contain 0.31 mass % HEOS meta borate ester and either 0.30 mass % triphenylphosphate (TPP) (Adpack H); 0.16 mass % of mixed phosphites (Adpack I); or 0.19 mass % dibutyl phosphite (DBP) (Adpack J). The three formulated oils were subjected to FZG and LMOT testing. The results are shown below:

TABLE 2

|  | H | I | J |
|---|---|---|---|
| Viscosity at 100° C. (cS) | 8.03 | 7.99 | 7.99 |
| LMOT at 320° F. (days to failure) | 10.5 | 9 | 10.5 |
| FZG (failure stage) | 9 | 10 | 12 |

The data of Table 2 demonstrates that an adpack containing HEOS meta borate ester (0.31 mass %), co-formulated with phosphorous-based friction modifiers, simultaneously provide antiwear and antioxidant properties in formulated oils.

Example 3

The antiwear properties of HEOS meta borate (0.31 wt. %)-dispersant combinations (PIBSA PAM (950 Mw polyisobutylene)) (3.5 wt. %), in which the HEOS-meta borate ester in an automatic transmission fluid (K) were compared to a fully formulated reference ATF (L) (containing no phosphorous-based, or other antiwear additives) in the industry standard Ford MERCON Vickers Pump Test (Ford Motor Company, MERCON Automatic Transmission Fluid Specification for Service, Mar. 5, 1987). The strong antiwear performance of the borate ester-dispersant combination, shown below in Table 3, was surprising given that the ATF contained no other antiwear additives. The data of Table 4 compares the measured Vickers Pump wear for the additized oil to the industry standards.

TABLE 3

| Additive Combination | FZG Failing Load Stage |
|---|---|
| K | 13 |
| L | 8 |

TABLE 4

| ATF Fluid Wear Result | GM Dextron III* Pass/Fail Limit |
|---|---|
| 12.mg Total Wear | 15 mg maximum Total Wear |

*Hydra-matic Division, General Motors Corp.

Example 4

To demonstrate the antiwear performance of the HEOS meta borate ester and dispersant combination in passenger car motor oils (PCMO), a PCMO containing 3.5 wt. % of a standard PIBSA-PAM clispersant (M) was compared to a PCMO containing the same dispersant and 0.28 wt. % HEOS-meta borate ester (N). Corrosive wear with the two samples was compared using the industry standard L38 Wear Test (ASTM D-5119), with the results being provided below in Table 5. As the data of Table 5 demonstrates, the addition of only 0.28 wt. % of the antiwear additive of the invention provided an approximately 50% improvement in the antiwear results.

TABLE 5

| Additive | L38 Wear Results (mg) |
|---|---|
| M | 56.7 |
| N | 25.8 |

Example 5

Lubricating oils are typically required to meet industry standards for oxidation performance. Antioxidants are normally added into these oils to prevent the oxidative degradation that normally occurs during usage. In PCMO and ATF lubricants, phosphorous compounds, such as ZDDP or phosphites, are often used for this purpose. The following tests demonstrate that the antioxidant effect of the HEOS meta borate ester antiwear additive of the present invention is sufficiently high to allow the formulation of an oil without an additional ZDDP or phosphite antioxidant.

An ATF containing Adpack N (described in Example 4) was subjected to a Ford MERCON Aluminum Beaker Oxidation Test (ABOT) (Ford MERCON method BJ110-4). The results achieved are compared to the industry standard limits in Table 6

TABLE 6

| ABOT | Result with Adpack N | Industry Limit |
|---|---|---|
| Δ total acid no. (TAN) | 1.28 | <4.0 |
| % viscosity increase @ 250 hrs. | 8.89 | <40% |
| Diff IR @ 250 hrs. | 22.2% | <40% |
| % pentane insol @ 250 hrs. | 0.53 | <1.0 |
| Cu Strip @ 300 hrs. | 3b | 3b max |

Example 6

The frictional properties of lubricating oils play a significant role toward improving fuel economy in automobiles. Use of friction reducers allows formulators to adjust the coefficient of friction to meet these needs. A combination of a HEOS meta borate ester and dispersant was found to provide excellent friction reducing characteristics. To demonstrate these friction reducing effects, a reference oil fully formulated with dispersant (5.5 wt. %), antifoamant, detergent, phosphorous-based antiwear/antioxidant and demulsifier additives, but containing no friction reducer, was compared to the same oil further formulated with 2.11 wt. % HEOS meta borate ester and 7.69 wt. % dispersant (Adpack O) using a High Frequency Reciprocal Rig(HFRR) test.

In the HFRR test, a metal disc is affixed to a platen within a bath. Opposite the platen, there is provided a vibrator arm to which a mass of 400 g is attached. A metal ball is affixed to the end of the vibrator arm. A sample of a lubricating oil is pipetted into the bath, immersing the disc and the vibrator arm is lowered so that the ball contacts the disc. The vibrator arm is then vibrated at a frequency of 20 Hz, with a stroke of 1000 microns. After each five minute period the temperature of the oil sample is increased 20°C. (6 steps from 40° C. to 140° C.). The disc is then removed from the platen, and the wear scar caused by contact with the ball is measured (diameters X and Y) using an optical microscope provided with a calibrated graticule.

TABLE 7

| Temperature (°C.) | Ref. Oil | Ref. Oil + Adpack O |
|---|---|---|
| 40 | 0.12 | 0.099 |
| 60 | 0.126 | 0.111 |
| 80 | 0.133 | 0.115 |
| 100 | 0.133 | 0.115 |
| 120 | 0.134 | 0.116 |
| 140 | 0.135 | 0.119 |

With the foregoing description of the invention, those skilled in the art will appreciate that modifications may be made to the invention without departing from the spirit thereof. Therefore, it is not intended that the scope of the invention be limited to the specific embodiments illustrated and described.

What is claimed:

1. A sulfur-containing boroester compound selected from the group consisting of:

alicyclic thioalkyl borate esters having the general formula (I):

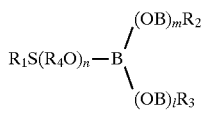

(I)

wherein $R_1$ is a hydrocarbyl radical having between about 4 to 12 carbon atoms, $R_2$ and $R_3$ are independently selected from the group consisting of $-(OR_4)_nSR_1$ and $-(OR_4)_nSR_1OH$; $R_4$ is a hydrocarbyl radical having between about 1 to 6 carbon atoms; n is an integer of from between about 1 to 4; and l and m are independently 0, 1 or 2, with the proviso that l and m are not both 0;

thioalkyl-substituted cyclic meta borate esters having the general formula (II):

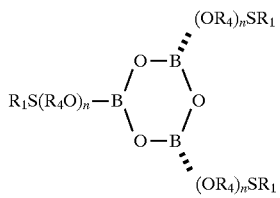

(II)

wherein n, $R_1$ and $R_4$ are defined as in formula (I); and mixtures of said alicyclic thioalkyl borate esters of formula (I) and said thioalkyl-substituted cyclic meta borate esters of formula (II).

2. The sulfur-containing boroester compound of claim 1, wherein said boroester is an alicyclic thioalkyl borate ester of formula (I); said $R_1$ is a hydrocarbyl radical having from between about 6 to 9 carbon atoms; said $R_4$ is a hydrocarbyl radical having from between about 2 to 4 carbon atoms; and l, m and n are all 1.

3. The sulfur-containing boroester compound of claim 2, wherein said $R_1$ is a hydrocarbyl radical having 6 carbon atoms; and said $R_4$ is a hydrocarbyl radical having 2 carbon atoms.

4. The sulfur-containing boroester compound of claim 1, wherein said boroester is a thioalkyl-substituted cyclic meta borate ester of formula (II); said $R_1$ is a hydrocarbyl radical having from between about 6 to 9 carbon atoms; and said $R_4$ is a hydrocarbyl radical having from between about 2 to 4 carbon atoms.

5. The sulfur-containing boroester compound of claim 4, wherein each $R_1$ is a hydrocarbyl radical having 6 carbon atoms; and each $R_4$ is a hydrocarbyl radical having 2 carbon atoms.

6. An oleaginous composition comprising a major amount of an oil selected from the group consisting of lubricating oils and power transmitting oils, and a minor amount of a sulfur-containing boroester compound selected from the group consisting of:

alicyclic thioalkyl borate esters having the general formula (I):

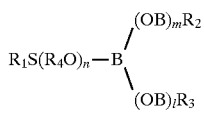

(I)

wherein $R_1$ is a hydrocarbyl radical having between about 4 to 12 carbon atoms, $R_2$ and $R_3$ are independently selected from $-(OR_4)_nSR_1$ and $-(OR_4)_nSR_1OH$; $R_4$ is a hydrocarbyl radical having between about 1 to 6 carbon atoms; n is an integer of from between about 1 to 4; and l and m are independently 0, 1 or 2, with the proviso that l and m are not both 0;

thioalkyl-substituted cyclic meta borate esters having the general formula (II):

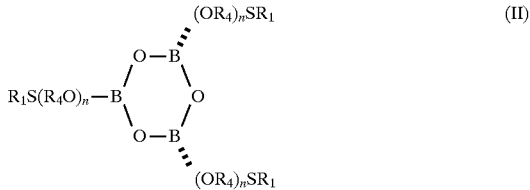

(II)

wherein n, $R_1$ and $R_4$ are defined as in formula (I); and mixtures of said alicyclic thioalkyl borate esters of formula (I) and said thioalkyl-substituted cyclic meta borate esters of formula (II).

7. The oleaginous composition of claim 6, wherein said sulfur-containing boroester compound comprises from between about 0.001 to 5 wt. % of said composition.

8. The oleaginous composition of claim 7, wherein said sulfur-containing boroester compound comprises from between about 0.02 to 1 wt. % of said composition.

9. The oleaginous composition of claim 6, wherein said sulfur-containing boroester compound is an alicyclic thioalkyl borate ester of formula (I); said $R_1$ is a hydrocarbyl radical having from between about 6 to 9 carbon atoms; said $R_4$ is a hydrocarbyl radical having from between about 2 to 4 carbon atoms; and l, m and n are 1.

10. The oleaginous composition of claim 9, wherein said $R_1$ is a hydrocarbyl radical having 6 carbon atoms; and said $R_4$ is a hydrocarbyl radical having 2 carbon atoms.

11. The oleaginous composition of claim 6, wherein said boroester is a thioalkyl-substituted cyclic meta borate ester of formula (II); said $R_1$ is a hydrocarbyl radical having from between about 6 to 9 carbon atoms; and said $R_4$ is a hydrocarbyl radical having from between about 2 to 4 carbon atoms.

12. The oleaginous composition of claim 11, wherein said $R_1$ is a hydrocarbyl radical having 6 carbon atoms; and said $R_4$ is a hydrocarbyl radical having 2 carbon atoms.

13. The oleaginous composition of claim 6, wherein said oil is at least one oil selected from the group of synthetic oils and natural oils.

14. The oleaginous composition of claim 6, further comprising at least one additive selected from the group consisting of: dispersants, viscosity modifiers, corrosion inhibitors, oxidation inhibitors, pour point depressants, anti-foaming agents, anti-wear agents, friction modifiers, detergents and rust inhibitors.

15. The oleaginous composition of claim 14, wherein said dispersant is a reaction product of polyisobutulene succinnic anhydride and a hydrocarbyl polyamine.

* * * * *